(12) United States Patent
Weldon et al.

(10) Patent No.: US 6,723,069 B1
(45) Date of Patent: Apr. 20, 2004

(54) ELECTROPHYSIOLOGY POSITIONING CATHETER

(75) Inventors: Thomas D. Weldon, Gainesville, GA (US); Charles E. Larsen, Cumming, GA (US); Jonathan J. Rosen, Alpharetta, GA (US)

(73) Assignee: Novoste Corporation, Norcross, GA (US)

( * ) Notice: Subject to any disclaimer, the term of this patent is extended or adjusted under 35 U.S.C. 154(b) by 141 days.

(21) Appl. No.: 09/609,854

(22) Filed: Jul. 5, 2000

Related U.S. Application Data (62) Division of application No. 08/530,466, filed on Sep. 19, 1995, now Pat. No. 6,139,522, which is a continuation of application No. 08/197,122, filed on Feb. 16, 1994, now abandoned.

(51) Int. Cl.[7] .............................................. A61M 31/00
(52) U.S. Cl. .......................... 604/93.01; 604/48; 604/35
(58) Field of Search .............................. 604/19, 21, 27, 604/30, 31, 35, 36, 37–38, 40–43, 48, 93.01, 118, 120–125, 146, 156, 158, 164.01, 164.02, 176, 268, 269, 523

(56) References Cited

U.S. PATENT DOCUMENTS

| | | | |
|---|---|---|---|
| 2,804,075 A | | 8/1957 | Borden |
| 3,048,175 A | | 8/1962 | Uddenberg |
| 3,429,313 A | * | 2/1969 | Romanelli ................. 604/43 |
| 3,952,743 A | * | 4/1976 | Harrison .................. 604/268 |
| 4,217,913 A | | 8/1980 | Dutcher |
| 4,393,883 A | | 7/1983 | Smyth et al. |
| 4,458,677 A | | 7/1984 | McCorkle, Jr. |
| 4,474,576 A | | 10/1984 | Gobby |
| 4,641,649 A | | 2/1987 | Walinsky et al. |
| 4,858,623 A | | 8/1989 | Bradshaw |
| 4,860,744 A | | 8/1989 | Johnson et al. |
| 4,881,542 A | * | 11/1989 | Schmidt et al. ............... 604/43 |
| 4,886,074 A | | 12/1989 | Bisping |
| 4,895,561 A | | 1/1990 | Mahurkar |
| 4,919,647 A | | 4/1990 | Nash |
| 5,147,355 A | | 9/1992 | Friedman et al. |
| 5,147,388 A | | 9/1992 | Yamazaki |
| 5,167,622 A | * | 12/1992 | Muto .......................... 604/35 |
| 5,179,961 A | | 1/1993 | Littleford et al. |

(List continued on next page.)

FOREIGN PATENT DOCUMENTS

| | | |
|---|---|---|
| DE | 2414578 | 3/1974 |
| DE | 3936811 | 11/1989 |
| DE | 4133298 | 10/1991 |
| EP | 416793 | 8/1990 |
| FR | 1460776 | 10/1965 |
| FR | 2365351 | 9/1976 |
| NL | 9200878 | 5/1992 |
| WO | WO87/4081 | 7/1987 |

OTHER PUBLICATIONS

Communication for the European Patent Office (Jun. 14, 1995) and European Search Report (May 22, 1995).

*Primary Examiner*—Manuel Mendez
*Assistant Examiner*—Michael M Thompson
(74) *Attorney, Agent, or Firm*—Cook, Alex, McFarron, Manzo, Cummings & Mahler, Ltd.

(57) ABSTRACT

Methods and apparatus are disclosed for treating body tissue whereby a section of tissue is drawn into contact with the open distal end of the first passageway of the apparatus. A tissue treatment fluid is introduced into the second passageway for treating the desired section of tissue retained within the first passageway. Methods and apparatus are also disclosed for positioning a medical device at a desired location within the heart. A portion of the apparatus is retained at a desired location of the heart and a medical device is extended through a passageway of the apparatus for contacting the heart at the desired location.

3 Claims, 6 Drawing Sheets

U.S. PATENT DOCUMENTS

| | | |
|---|---|---|
| 5,188,595 A | 2/1993 | Jacobi |
| 5,195,942 A | 3/1993 | Weil et al. |
| 5,255,679 A | 10/1993 | Imran |
| 5,259,395 A | 11/1993 | Li |
| 5,267,960 A | 12/1993 | Hayman et al. |
| 5,312,341 A | 5/1994 | Turi |
| 5,342,295 A | 8/1994 | Imran |
| 5,360,416 A | 11/1994 | Ausherman et al. |
| 6,139,522 A * | 10/2000 | Weldon et al. ............... 604/48 |

* cited by examiner

ELECTROPHYSIOLOGY POSITIONING CATHETER

This is a divisional application of U.S. patent application Ser. No. 08/530,466, filed on Sep. 19, 1995 now Pat. No. 6,139,522, which is a continuation of U.S. Ser. No. 08/197,122, filed on Feb. 16, 1994, now abandoned.

FIELD OF THE INVENTION

The present invention generally relates to catheters for use in the diagnosis or treatment of disorders found in bodily tissues in general and heart tissue in particular. More specifically, the present invention relates to novel methods and catheter apparatus for isolating and treating a selected tissue site and to novel methods and apparatus for providing a stable base for positioning a medical device at a selected location within the heart for diagnosing or treating heart tissue.

BACKGROUND ART

Catheters and catheter-like devices have been used for many years in the diagnosis or treatment of various disorders or conditions within the human body. It is become commonplace, for example, to introduce catheters through the vascular system of patient in order to diagnose or treat conditions within the human heart.

One example of a catheter for treating body tissue is described in U.S. Pat. No. 4,860,744. The medical catheter described therein is used in treating internal tumors or other growths located on the internal body tissue of a patient. The catheter is inserted into the patient's body and is advanced to the area to be treated. X-rays allow the physician to monitor the progress of the catheter through the patient's body. Once the tip of the catheter reaches the area of tissue to be treated, the catheter tip is heated and applied to the tumor so as to eliminate it.

Another catheter and catheterization method are described in U.S. Pat. No. 5,147,355. The catheter in that patent is also guided through a patient's blood vessels to a location within the patient's body, such as the area of the heart, so that the tip of the catheter is adjacent to the area of tissue to be treated. Once in place, the tip of the catheter is cryogenically cooled and applied to the selected area of tissue. Applying the super-cold tip of the catheter ablates the area of tissue.

A catheter for treating disorders associated with the conduction of electrical signals, in cardiac tissue is described in U.S. Pat. No. 4,641,649. The catheter described therein includes an antenna located at the distal tip of the catheter. The antenna receives electrical signals from the heart and transmits them to a recording device, thus purportedly allowing the physician to determine the source of the cardiac disorder. Once the source has been located, radio frequency or microwave frequency electrical energy is applied to the section of tissue through the tip of the catheter to eliminate the source of the electrical disorder.

Although the use of catheters for diagnosing and treating medical conditions has been long accepted, one pervasive problem is in anchoring and retaining the catheter tip at the desired section of body tissue. This problem is most common when treating organs that are subjected to repeated movements such as the heart. As described in detail below, the continuous movement of the heart muscle and pulsating flow of blood therethrough often makes it difficult for a physician to position and retain the catheter tip at a selected site within the heart long enough to perform the desired treatment procedure (e.g. ablation) or diagnosis.

The human heart has four chambers for receiving blood and for pumping it to various parts of the body. In particular, the two upper chambers of the heart are called atriums, and the two lower chambers are called ventricles.

During normal operation of the heart, oxygen-poor blood returning from the upper and lower extremities of the body enters the upper right chamber known as the right atrium. The right atrium fills with blood and eventually contracts to expel the blood through the tricuspid valve to the lower right chamber known as the right ventricle. As the right atrium relaxes, blood fills the right ventricle. Contraction of the right ventricle ejects the blood in a pulse-like manner from the right ventricle to the pulmonary artery which divides into two branches, one going to each lung. As the oxygen-poor blood travels through the lungs, it becomes oxygenated (i.e. oxygen-rich).

The oxygenated blood leaves the lungs through the pulmonary veins and fills the upper left chamber of the heart known as the left atrium. When the left atrium contracts, it sends the blood through the mitral valve to the lower left chamber called the left ventricle. Contraction of the left ventricle, which is the stronger of the two lower chambers, forces blood through the main artery of the vascular system known as the aorta. The aorta branches into many smaller arteries and blood vessels that eventually deliver the oxygen-rich blood to the rest of the body.

Typically, diagnosis or treatment of cardiac disorders, such as cardiac arrythmia, requires introducing a catheter into the heart as disclosed, for example, in U.S. Pat. Nos. 5,147,305 and 4,641,649. However, as described above, the constant contraction and relaxation of the heart muscle, together with the pulsating flow of blood therethrough, makes accurate placement of catheter difficult even in the best of circumstances.

Because of the difficulty in accurately positioning and retaining the tip of the catheter tip at the desired location in a pumping heart, there exists today a need for suitable methods and/or apparatus that will allow the physician to anchor and retain the catheter tip at the desired location in the heart or other body tissue during the treatment or diagnosis.

SUMMARY DISCLOSURE OF THE INVENTION

The present invention is directed, in part, to an apparatus for treating body tissue. The apparatus comprises an elongated tubular body portion that has a proximal end portion and a distal end portion. A first passageway extends through the tubular body portion between the proximal end portion and the distal end portion and has an open distal end. The apparatus includes means for drawing a desired section of tissue into contact with the open distal end of the first passageway so as to isolate the section of tissue. A second passageway also extends through the tubular body portion between the proximal and the distal end portions. The second passageway is in fluid communication with the first passageway at a location sufficiently proximate to the distal end portion so that when a treating fluid is introduced through the second passageway and flows into the first passageway, the fluid comes into contact with the tissue drawn into the open distal end portion of the first passageway. The fluid is withdrawn through the first passageway. Thus, the device is anchored at a particular location of tissue, which helps prevent inadvertent dislocation of the catheter tip by movement of the tissue or body fluids. Also, the contact between the distal end portion of the catheter and the section of tissue isolates the tissue section from the rest of the body. This allows fluid to be used to treat a desired section of tissue without generally introducing the fluid into the body or unnecessarily exposing other parts of the body to the fluid.

More particularly, the present invention is directed to an apparatus for positioning a medical device within the heart. The apparatus includes an elongated tubular body that has proximal end and a distal end portion. A passageway extends through the tubular body between the proximal end and the distal end portion and is open at the distal end portion. The apparatus also includes means for retaining the distal end portion of the apparatus at a desired location of the heart. A medical device, suitable for contacting the heart at the desired location may be inserted into the passageway exiting through the opening in the distal end portion. With the retaining means securing the tubular body at the desired section of tissue, the medical device may be positioned at a particular location for treating or diagnosing heart conditions despite the continuous movement of the heart and pulsating movement of blood therethrough.

The present invention is also directed to a method for treating body tissue. The method includes providing a catheter that has proximal end portion, a distal end portion, and first and second passageways extending between the proximal end the distal end portions. The first passageway has an open distal end and the first and second passageways are in flow communication with each other proximate to the distal end portion. In accordance with the method, the open distal end of the first passageway is placed over a desired section of tissue. The section of tissue is drawn into contact with the open distal end of the first passageway so as to isolate the desired section of tissue. Fluid is introduced through the second passageway to contact or treat the selected area of tissue and is withdrawn through the first passageway.

Further, the present invention is directed to a method for firmly positioning a medical device within the heart. The method includes providing a catheter that has a proximal end portion, a distal end portion, and at least one passageway extending between the proximal end and the distal end portion, the passageway being open at the distal end portion. The method for positioning a medical device within the heart also includes the step of locating the distal end portion of the catheter at a selected position within the heart and securing the distal end portion to the heart tissue at the selected position. This maintains the distal end of the catheter at a relatively stable, fixed position despite heart movement and allows introduction of a medical device into the passageway and through the proximal end for contacting the desired section of heart tissue through the open distal end portion of the passageway.

These and other features of the present invention are set forth in the following detailed description of the accompanying drawings.

DETAILED DESCRIPTION OF THE INVENTION

Figures 1, 2, 4:
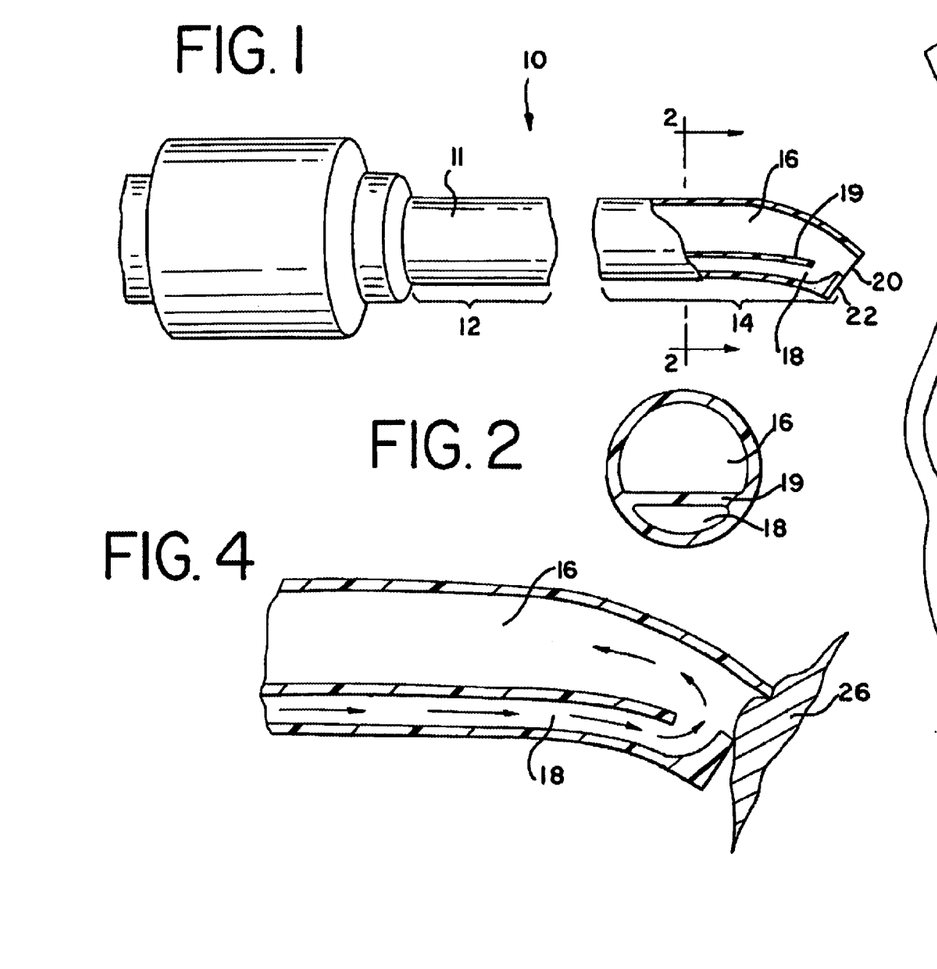
FIG. 1 is a perspective view, partially broken away, of the apparatus of the present invention.
FIG. 2 is a transverse cross-sectional view along line 2—2 of the apparatus of FIG. 1.
FIG. 4 is a longitudinal cross-sectional view of the distal end of the apparatus shown in FIG. 1.

Turning now to the drawings, FIG. 1 depicts a catheter or catheter-type medical instrument 10 embodying features of the present invention.

In the embodiment shown in FIG. 1, catheter 10 includes an extruded, elongated, polymeric tube 11 having a proximal end portion 12 and a distal end portion 14. As used in connection with this and the other embodiments disclosed, "distal end portion" generaly means a length of the catheter tubing extending up to and including the distal tip. Specifically, for catheters and catheter-type devices used for treating heart tissue, the term "distal end portion", as used herein, is understood to mean that portion of the catheter or catheter-type device which extends into the heart. As seen in FIG. 1, catheter 10 has a first passageway 16 that extends through the polymeric tube from proximal end 12 to the distal end portion 14. A second passageway 18 also extends through the polymeric tube 11 from the proximal end 12 to the distal end portion 14 parallel to passageway 16. Common wall 19 extends substantially along the length of the tube 11 between the first and second passageways. Passageway 16 terminates in an open distal end 20. Passageway 18 is occluded, such as by a post-extrusion sealing, at the distal end tip 22 of the catheter 10 but communicates with passageway 16 through an opening in common wall 19 near open distal end 20. As seen in FIG. 2, first passageway 16 has a substantially larger cross-sectional area than passageway 18.

Figure 2A:
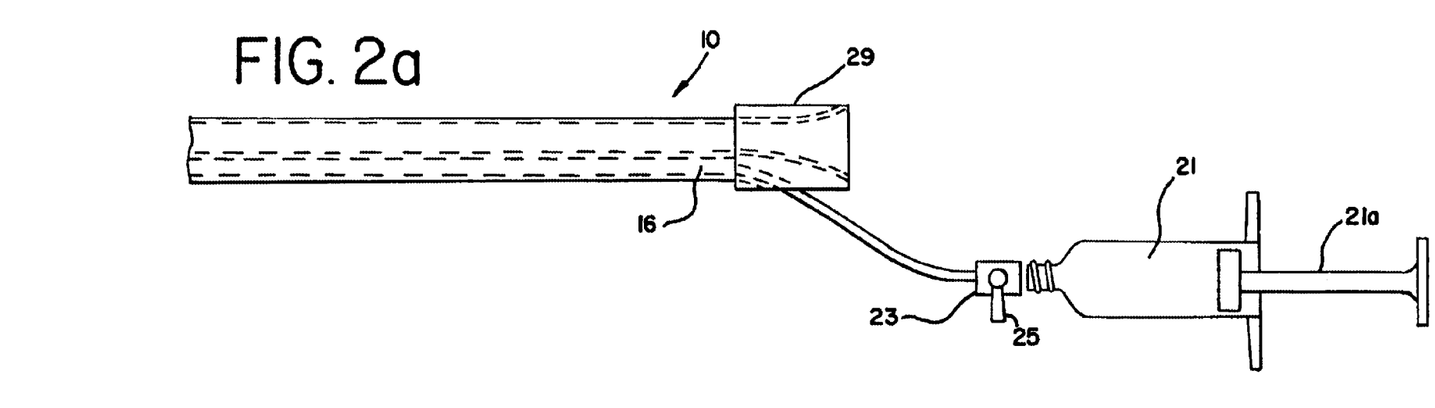
FIG. 2a is a perspective view of the proximal end of one or more embodiments of the present invention.

A source of suction such as a syringe or a vacuum pump may be associated with the first passageway 16. For example, as generally depicted in FIG. 2a, syringe 21 may be attached to passageway 16 at the proximal end of catheter 10 near luer lock hub 23. Luer lock hub 23 also includes stopcock 25. With stopcock 25 in the "open" position and by withdrawing plunger 21a of syringe 21, a suction force within passageway 16 is established. Stopcock 25 is then turned to the closed position to maintain the suction force and, thereby, firmly secure catheter tip to the tissue. As depicted in detail in FIG. 4, by introducing a suction force through passageway 16, a desired section of body tissue is drawn into open distal end 20 of catheter 10 so as to isolate the section of tissue.

Figure 2B:
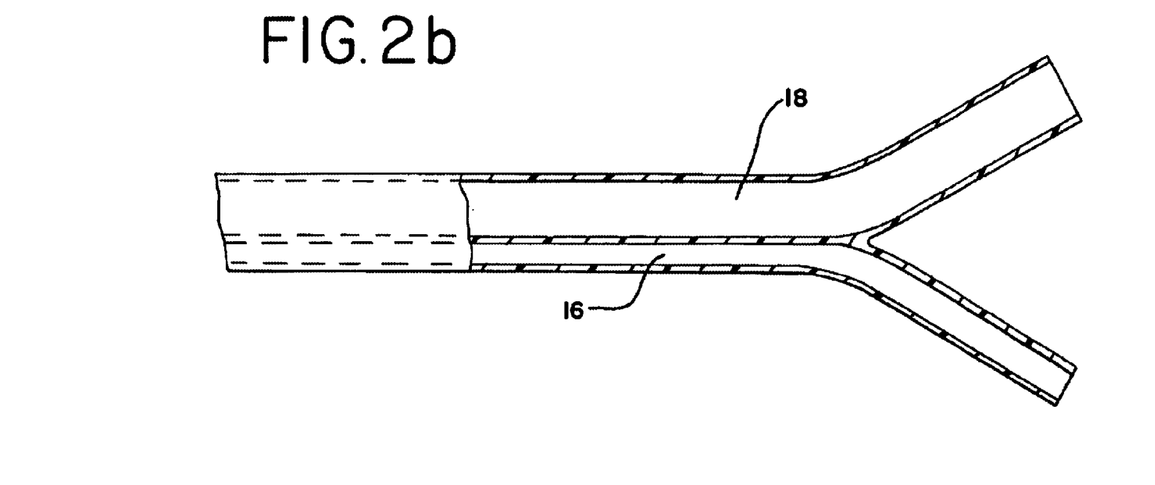
FIG. 2b is a detailed view of a portion of the proximal end of one or more embodiments of the present invention.

Passageway 18 is attached to a controllable source of medical fluid (not shown) near proximal end portion 12 of passageway 18. The medical fluid or drug may be introduced into second passageway 18 directly or through hub 29 shown in FIG. 2a. Hub 29 may be bifurcated, as shown in FIG. 2b, so as to keep the proximal ends of passageways 16 and 18 separated from each other. Regardless of how the medical fluid is administered, fluid is introduced into passageway 18 and travels from the proximal end 12 to the distal end portion 14 and through the opening in common wall 19. As fluid enters passageway 16 through the opening in common wall 19, it contacts the section of tissue drawn into open distal end 20. The fluid and any loose tissue debris exits the catheter through passageway 16.

Although suitable for treating various different body tissues, the catheter of the present invention finds particular application in the treatment of internal body tissue such as heart tissue. In accordance with the method for treating heart tissue, a catheter of the type described above is introduced percutaneously into the vascular system of the patient and advanced to the area of the heart in a manner well known to those skilled in the art of catheterization. Typically, catheter 10 is inserted through a selected vein or artery (e.g. femoral) and directed through the circulatory system (not shown) of the patient until it eventually enters the heart. Catheter 10 may be introduced into and guided through the body by using, for example, a sheath or guide wire. Alternatively, catheter 10 may be directly introduced and guided through the body without any such guiding device.

Figure 3:
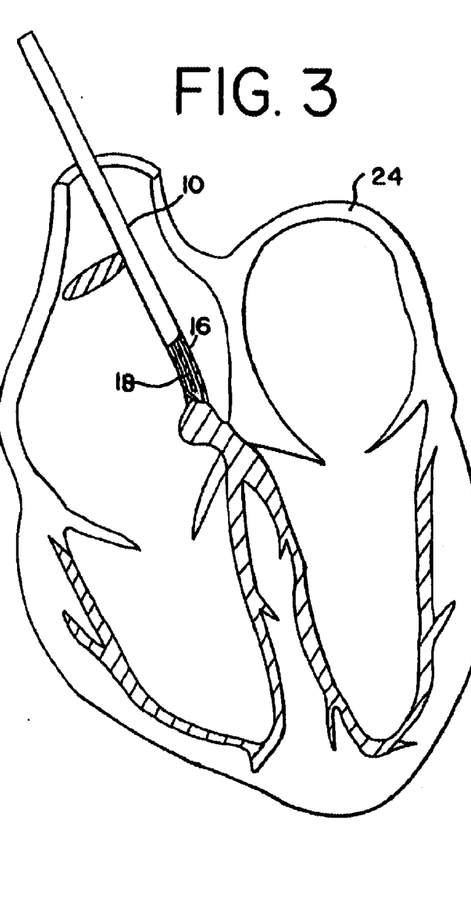
FIG. 3 is a cross-sectional view of a human heart with the distal end of the apparatus of the apparatus of FIG. 1 disposed within the right atrium of the heart.

FIG. 3 shows the distal end of the catheter 10 inside a portion of a human heart 24. The tip of the catheter 10 is positioned so that opening 20 in passageway 16 is located over the section of tissue to be treated or diagnosed. The position of the catheter tip may be monitored by using an x-ray as described in U.S. Pat. No. 4,641,649. Once the desired section of heart tissue is located, a suction force is applied through passageway 16 so as to draw the desired section of tissue into the open distal end 20. The source of the suction may be pre-attached to catheter 10 or may be attached by the physician once the tip of the catheter is located at the desired section of tissue. The suction force may be applied by withdrawing the plunger of a syringe or by another vacuum source, such as a vacuum pump as described, for example, in connection with FIG. 2a. The suction force holds the section of heart tissue tightly within the distal end of the first passageway, simultaneously retaining the distal end at that location and sealing off or isolating the section of tissue within the distal end from the rest of the tissue to permit treating of the selected section tissue if desired.

FIG. 4 shows the distal end of catheter 10 in contact with a section of heart tissue 26. As can be seen in FIG. 4, the open distal end 20 of passageway 16 is positioned against the tissue 26. The suction force applied through passageway 16 draws, retains, and isolates the desired section of tissue 26 into the open distal end 20 of passageway 16.

After suction has been applied and the desired section of tissue 26 isolated, the section of tissue 26 may be treated or ablated with an appropriate drug or other fluid introduced at the proximal end of the second passageway 18. As the fluid travels down the passageway 18 toward the distal end portion of the catheter, it is diverted by the occluded end 22, through opening 19 and into passageway 16. There, the fluid contacts the section of heart tissue drawn into the open distal end 20 of passageway 16. The fluid and any loose debris is drawn out through passageway 16 by the suction force. After completion of the treatment, the drug or medical fluid may be replaced with saline or other solution so as to rinse the catheter 10 (and the isolated section of tissue). After rinsing, the suction force is turned off and the catheter 10 is removed. Thus, a specific section of tissue may be treated with the medical fluid or drug without allowing the fluid to enter the body generally or contact any tissue other than the desired tissue.

This feature of the present invention has many benefits. For example, by isolating the particular tissue section and by not allowing the treating fluid to generally escape into the body, treating fluids may be used that perhaps wold not ordinarily be used because of possible adverse affects on other parts of the body. There may also be benefits, not yet foreseen, to the ability to place a treating fluid, such as a medicament or the like, at a specific location only.

Figure 5:
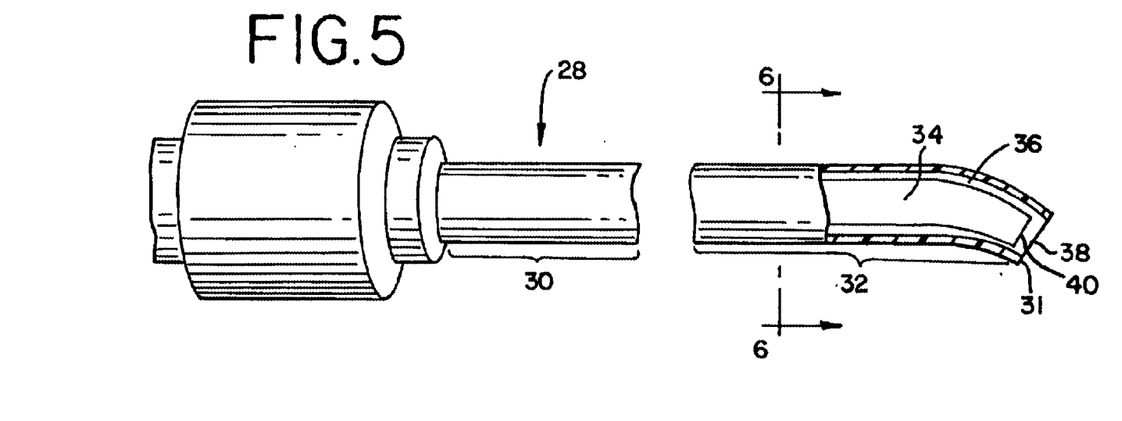
FIG. 5 is a perspective view, partially broken away, of another embodiment of the apparatus of the present invention.
Figure 6:
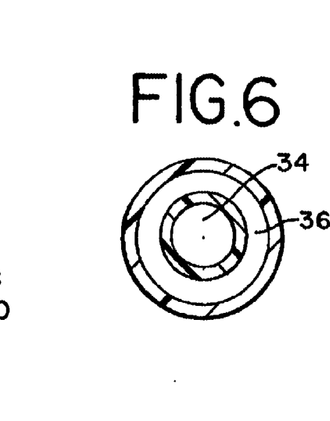
FIG. 6 is a transverse cross-sectional view along line 6—6 of the apparatus of FIG. 5.

An alternative embodiment of the present invention is shown in FIG. 5. Like the preferred embodiment described above and depicted in FIGS. 1–2, catheter 28 includes an elongated, extruded, polymeric tube having a proximal end 30 and a distal end portion 32. The catheter 28 includes a first passageway 34 and a second passageway 36. As shown in FIG. 6, passageways 34 and 36 are coaxial. Passageway 36 of catheter 28 is open at the distal tip 1 of catheter 28. Passageway 34 is also open at end 40 but does not extend to the distal tip 31 of distal end portion 32.

Figure 7:
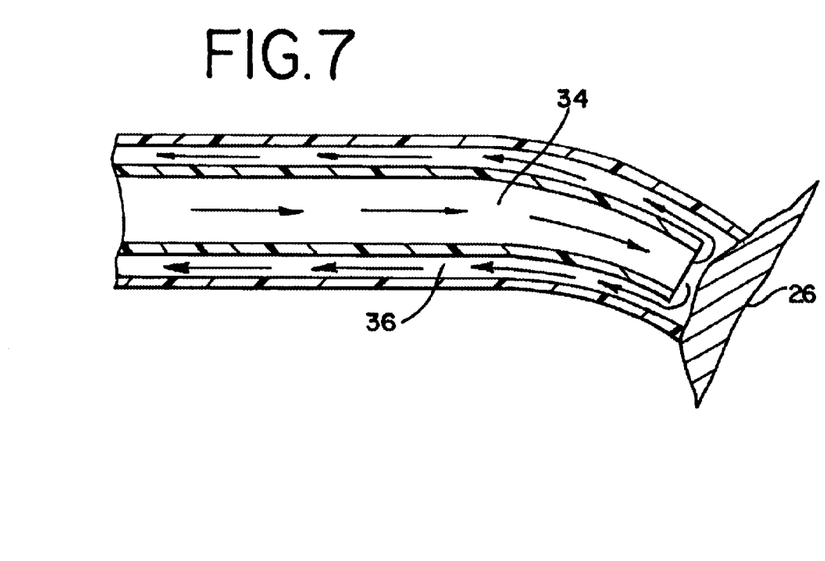
FIG. 7 is a longitudinal cross-sectional view of the distal end of the apparatus of FIG. 5.

The catheter 28 may be used in substantially the same way as the method for treating body tissue described above and depicted in FIGS. 1–4. Catheter 28 is introduced into the body of a patient and directed to the section of heart tissue to be treated by using, for example, a sheath, guide wire or no guiding device at all. Distal tip 31 is positioned over the desired section of tissue and as shown in FIG. 7, is brought into contact with a section of heart tissue 26. As described above, a suction force is applied through one of the two passageways. In this embodiment, the suction force is applied through outer passageway 36. The suction force draws a section of heart tissue 26 into the open end 38 of the distal end portion 32 and isolate the section from the rest of the tissue. A drug or other medical fluid is then introduced through center passageway 34, thereby directly administering the fluid to the isolated section of heart tissue 26. The medical fluid or drug is then removed through passageway 36 by the suction force applied therethrough.

Figure 8:
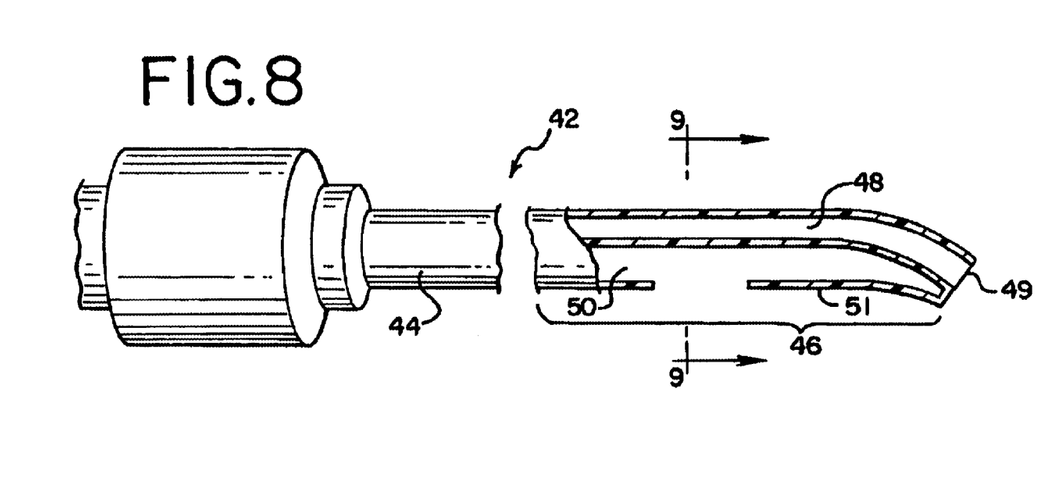
FIG. 8 is a perspective view, partially broken away, of yet another embodiment of the apparatus of the present invention.
Figure 9:
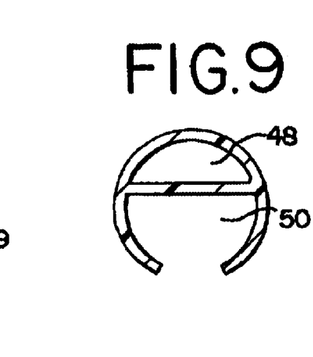
FIG. 9 is a transverse cross-sectional view along line 9—9 of the apparatus of FIG. 8.
Figure 10:
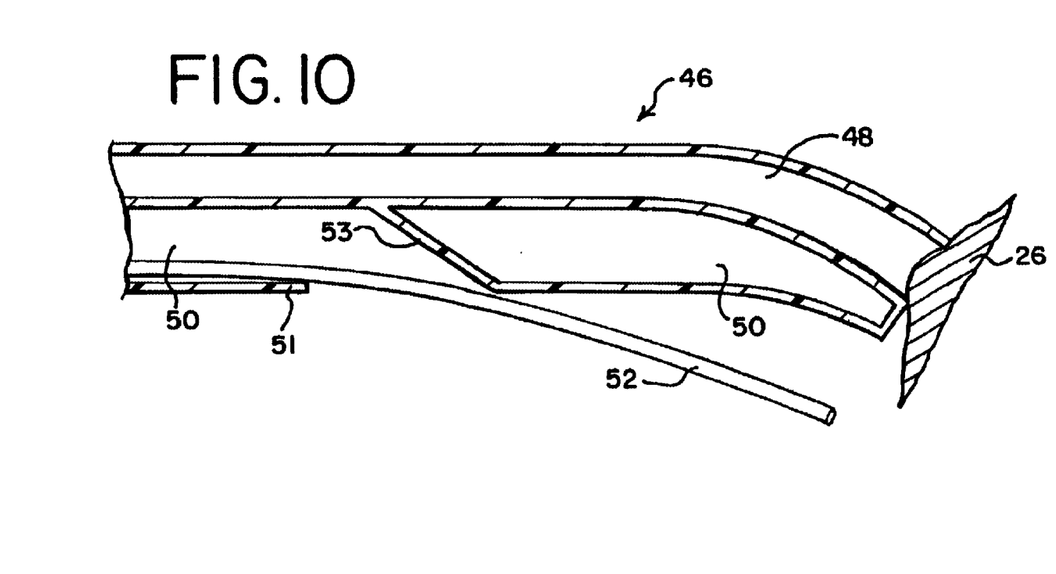
FIG. 10 is a longitudinal cross-sectional view of the distal end of the apparatus of FIG. 8.

FIGS. 8–10 show a third embodiment of the present invention. Like the embodiments described above, the catheter 42 shown in FIG. 8 includes a polymeric tube having a proximal end 44 and a distal end portion 46. Catheter 42, includes a first passageway 48 and a second passageway 50. Passageway 48 has an open distal end tip 49 whereas passageway 50 is occluded at the distal-most end of the catheter. Passageway 50, however, includes an opening in outer catheter wall 51 at a location spaced from the distal end tip 49 of the catheter 42, but generally within the distal end portion 46. The passageways 48 and 50 may be sized as needed for the suction and/or medical instrument to be inserted. As shown in FIG. 9, it is preferred that the cross-sectional area of the second passageway 50 be larger than the cross-sectional area of the first passageway 48 or, at least, large enough to accommodate a second "working" catheter as described below.

In accordance with the method of treating body tissue generally, and heart tissue in particular, catheter 42 is introduced into the body of a patient and advanced to the area of the heart. As described above in connection with earlier embodiments, catheter 42 may be advanced by using a sheath, guide wire or no guiding device whatsoever. The distal end tip 49 of the distal end portion 46 is brought into contact with the section of tissue to be treated. FIG. 10 shows the distal end portion 46 of catheter 42 in contact with a section of heart tissue 26. As in the above-described embodiments, a suction force is applied through passageway 48. The suction force draws the section of tissue 26 into open distal end tip 49 of passageway 48, holding the distal end in a stable position within the heart. Once the section of tissue 26 is firmly secured to the catheter 42, a second catheter or diagnostic or surgical device 52 is then inserted through the passageway 50. Catheter 42 may also include the hub with or without the bifurcated passageway arrangement, as described previously in connection with FIGS. 2a and 2b, through which surgical device 52 is introduced. In any event, surgical device 52 extends through the passageway 50 and exits passageway 50 through an opening in side wall 51. Device 52 may be any catheter or medical device used for diagnosing or treating tissue such as the catheters described in U.S. Pat. Nos. 4,860,744 and 5,147,355. A rigid or hinged chute or slide 53 may be attached to the catheter near opening in side wall 51 to assist in directing the second catheter to its desired location. Alternatively, surgical device 52 may extend through passageway 48 and suction may be applied through passageway 50 so as to anchor distal end portion 46 to the body tissue 26 at the opening in catheter wall 51.

Thus, apparatus 42 serves as the "positioning" catheter which provides an anchored pathway for the second "working" catheter 52. Providing an anchored pathway for the "working" catheter ensures that the drug or medical treatment or diagnosis will occur at the desired location of the tissue, despite movement of the heart or flow of blood. It also provides means for accurately positioning commercially available catheters and surgical instruments that do not otherwise have means for securely holding the tip of the instrument in place.

Figure 11:
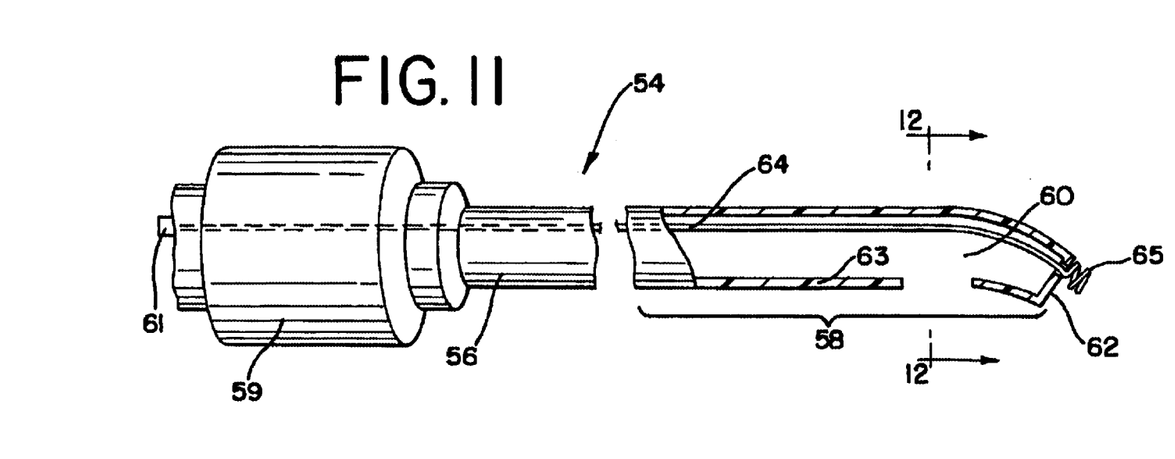
FIG. 11 is a perspective view, partially broken away, of another embodiment of the apparatus of the present invention.
Figure 12:
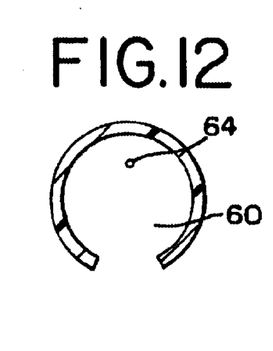
FIG. 12 is a transverse cross-sectional view along line 12—12 of the apparatus shown in FIG. 11.
Figure 13:
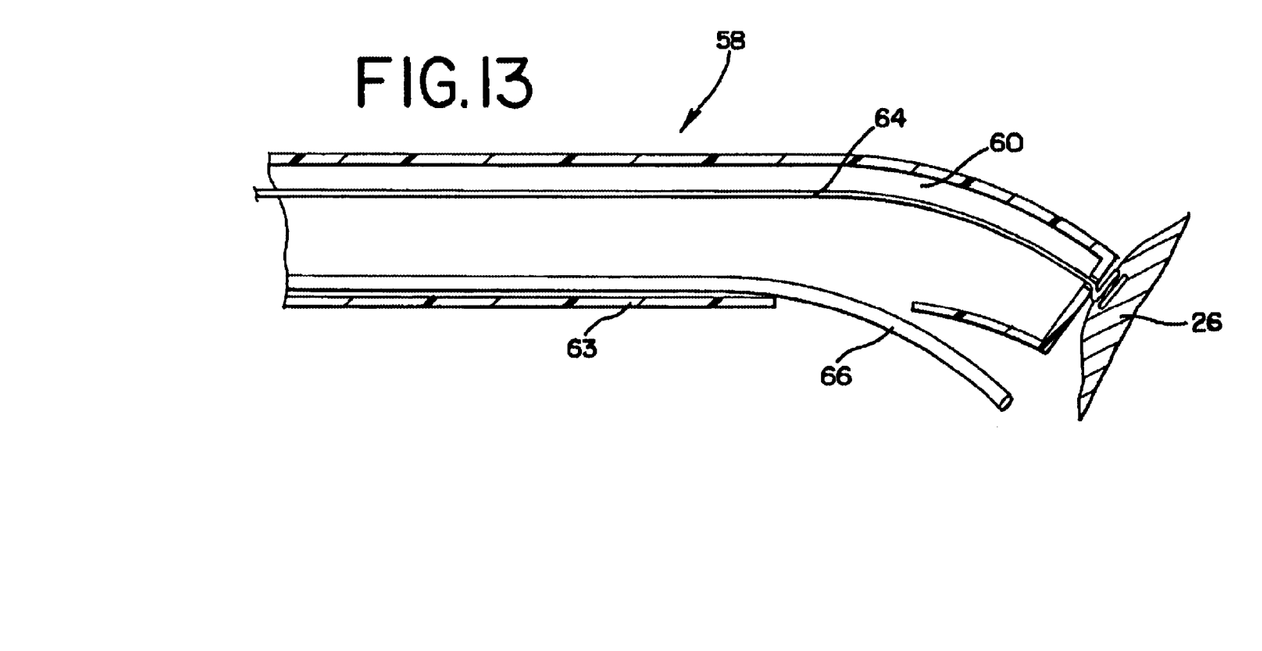
FIG. 13 is a longitudinal cross-sectional view of the distal end of the catheter shown in FIG. 11.

FIGS. 11–13 show a fourth embodiment of the present invention. In FIG. 11, a positioning catheter 54 similar to the positioning catheter described in FIGS. 8–10 is shown. Catheter 54 includes an elongated polymeric tube having a proximal end 56 and a distal end portion 58. Catheter 54 includes a single passageway 60 that is occluded at its distal end tip 62 but includes an opening in side wall 63 spaced from the distal tip of the catheter. Catheter 54 further includes wire 64, the distal end of which has been conformed into an attachment device 65 such as a hook or corkscrew for securing the distal end tip 62 of catheter 54 to the tissue. Alternatively, attachment device 65 may comprise a separate piece connected to wire 64. Wire 64 extends along the top inner surface of passageway 60, through hub 59 and is attached at its proximal end to knob 61. During operation of catheter 54, rotation of knob 61 turns wire 64 with attachment device 65, thereby causing attachment device 65, which is located on the outer surface of catheter 54, to penetrate the section of tissue and secure catheter 54 to the tissue. Alternatively, the distal end tip 62 of catheter tip may be equipped with an inflation device, such as a balloon for atraumatically anchoring the catheter.

In accordance with the method of treating body tissue, catheter 54 is introduced into the body of the patient and the distal end portion 58 of the catheter 54 is advanced (as described above) to a location near the section of tissue to be treated or diagnosed. The distal end tip 62 is then gently brought into contact with the tissue so as to cause shallow penetration of the heart tissue 26 by attachment device 65 located at the distal tip 62. By firmly securing the section of tissue 26 to the distal tip of catheter 54 in the manner described above, an anchored pathway for a second "working" catheter is provided. The second "working" catheter 66 or other surgical tool (as described above) is then introduced into passageway 60 of catheter 54. Working catheter 66 is directed through passageway 60 and the opening in catheter wall 63 to the section of tissue to be treated or diagnosed.

Figure 14:
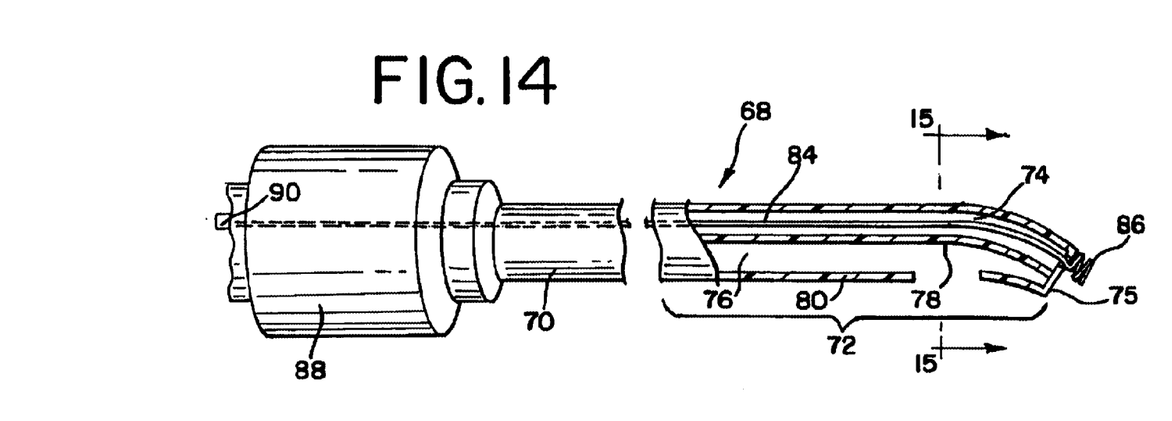
FIG. 14 is a perspective view, partially broken away, of another embodiment of the apparatus of the present invention.
Figure 15:
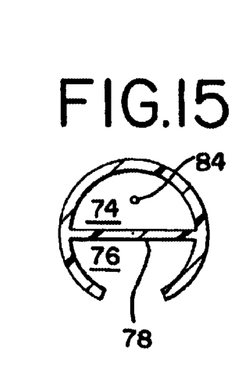
FIG. 15 is a transverse cross-sectional view along line 15—15 of the apparatus shown in FIG. 14.
Figure 16:
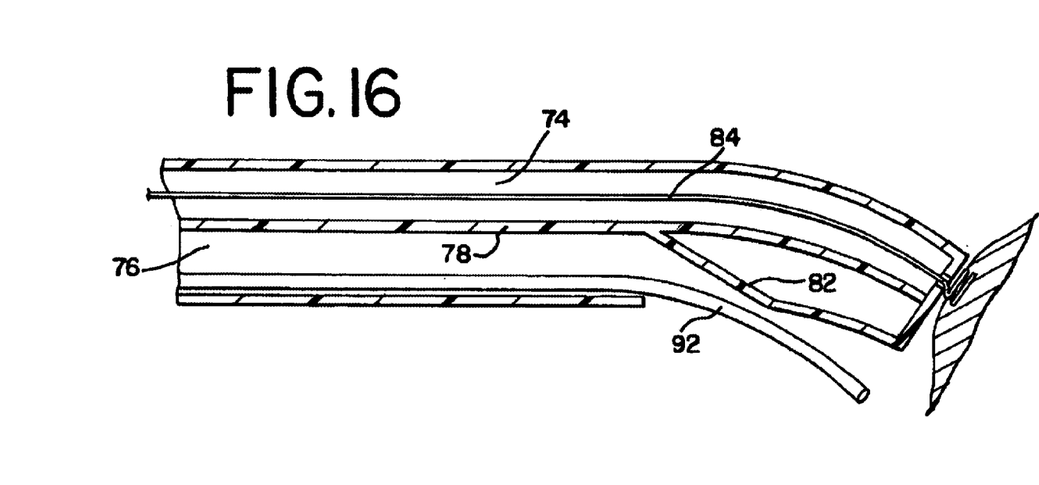
FIG. 16 is a longitudinal cross-sectional view of the distal end of the catheter shown in FIG. 14.

Finally, FIGS. 14–16 show a fifth embodiment of the present invention. In FIG. 14, a positioning catheter 68 similar to the positioning catheter described in connection with FIGS. 8–10, but utilizing an attachment device as described above in connection with FIGS. 11–13, is shown. Catheter 68 includes an elongated polymeric tube having a proximal end 70 and a distal end portion 72. Catheter 68 includes a first passageway 74 and a second passageway 76, separated by wall 78. Both passageways 74 and 76 are occluded at the distal end tip 75. Passageway 76, however, includes an opening in outer catheter wall 80 at a location spaced from the distal end tip 75 of the catheter 68, but within the distal end portion. A rigid or hinged chute or slide 82 may be attached to the catheter near opening in side wall 80 to assist in directing a second "working" catheter to its desired location.

Passageway 74 includes wire 84 with an attachment device 86 at the distal end of wire 84. As described above, attachment device 86 may be provided by forming the distal end of wire into the desired shape (e.g. hook, corkscrew). Alternatively, attachment device 86 may be separately connected to wire 84. Wire 84 extends along the length of passageway 74, through hub 88, and is attached at its proximal end to knob 90. As described above in connection with FIGS. 11–13, rotating knob 90 turns wire 84 with attachment device 86, thereby causing attachment device 86 to penetrate the section of tissue and secure the catheter tip to the body tissue. With the catheter 68 firmly anchored to the tissue, a second "working" catheter 92 may be introduced into passageway 76.

Although the present invention has been described in terms of the preferred embodiment, various modifications, some immediately apparent, and others apparent only after some study, may be made without departing from the present invention. The scope of the present invention is not to be limited by the detailed description of the preferred embodiment but, rather, is to be defined by the claims appended below.

That which is claimed:

1. Apparatus for in situ treatment of body tissue comprising:

a) a flexible, polymeric tube adapted for advancement through the vascular system of a patient comprising an elongated tubular body portion having a proximal end portion and a distal end portion terminating in a distal tip, said polymeric tube including:

i) a first fluid removing passageway extending through said tubular body portion between said proximal end and said distal end portion, said passageway being open only at the distal tip of said tube;

ii) a second fluid delivering passageway extending through said tubular body portion between said proximal end and said distal end portion and parallel to said first passageway, said second passageway being occluded at said distal tip of said tubular body portion and in fluid communication with said first passageway sufficiently proximate to said distal tip to direct fluid to the tissue to be treated, whereby fluid may be introduced into said second passageway for contact with the tissue drawn into the open distal tip of said first passageway and then withdrawn through said first passageway;

b) a suction device for temporarily drawing a desired section of body tissue into contact with said open distal tip of said first passageway so as to isolate said section of tissue and anchor said distal end portion at the isolated section of tissue and anchor said distal end portion at the isolated section of tissue.

2. The apparatus of claim 1 wherein said suction device is selected from the group consisting of a syringe and a vacuum pump.

3. The apparatus of claim 1 wherein said first passageway has a larger cross-section than said second passageway.

* * * * *